United States Patent
Brumlik

(10) Patent No.: US 11,602,610 B2
(45) Date of Patent: Mar. 14, 2023

(54) CHAIN MAIL MESH AND PROCESS FOR REDUCING STRESS

(71) Applicant: Charles Joseph Brumlik, Branchburg, NJ (US)

(72) Inventor: Charles Joseph Brumlik, Branchburg, NJ (US)

(*) Notice: Subject to any disclaimer, the term of this patent is extended or adjusted under 35 U.S.C. 154(b) by 66 days.

(21) Appl. No.: 17/120,182

(22) Filed: Dec. 13, 2020

(65) Prior Publication Data
US 2021/0178114 A1    Jun. 17, 2021

Related U.S. Application Data

(60) Provisional application No. 62/947,554, filed on Dec. 13, 2019.

(51) Int. Cl.
*A61M 21/00*    (2006.01)
*A61M 21/02*    (2006.01)

(52) U.S. Cl.
CPC ..... *A61M 21/02* (2013.01); *A61M 2021/0022* (2013.01)

(58) Field of Classification Search
CPC ................ A61M 21/02; A61M 2021/0022
See application file for complete search history.

(56) References Cited

U.S. PATENT DOCUMENTS

| | | |
|---|---|---|
| 4,564,539 A | 1/1986 | Tsuji |
| 7,501,069 B2 | 3/2009 | Liu |
| 7,527,845 B2 | 5/2009 | King |

(Continued)

FOREIGN PATENT DOCUMENTS

| | | |
|---|---|---|
| DE | 102015226063 A1 | 6/2017 |
| DE | 102018130205 A1 | 5/2018 |
| EP | 1920108 B1 | 2/2014 |

OTHER PUBLICATIONS

Screen captures and YouTube video clip entitled "3D Printed Chainmail—IT'S ACTUALLY WORKING???" 2 pages, uploaded on Feb. 27, 2019 by user "Jazza Studios", time 3:00-3:50. Retrieved from Internet: https://www.youtube.com/watch?v=iZLrurXtYX4 (Year: 2019).*

(Continued)

*Primary Examiner* — Kaylee R Wilson

(57) ABSTRACT

A chain mail mesh comprising interconnecting, polygonal links suitably interconnected to define a sheet having each of the interconnecting, polygonal links having at least one degree of freedom of movement in at least one direction with respect to its neighbouring polygonal links wherein each of the interconnecting, polygonal links, interconnected to at least one neighbouring interconnecting polygonal link, combine to form an operative upper surface and an operative lower surface of the sheet, and wherein at least a portion of at least one of the operative upper surface and the operative lower surface of the sheet generally feels smooth with gaps, which produce a calming or pleasing effect when contacted with or moved over, or combinedly contacted with and moved over a human's body portion which being apt to sense of touch. The sheet has a predetermined drape coefficient, nonlinear motion, and is capable of providing relief in stress or pleasure when a human employs the same.

12 Claims, 8 Drawing Sheets

(56) References Cited

U.S. PATENT DOCUMENTS

| | | |
|---|---|---|
| 7,591,928 B2 | 9/2009 | Billings |
| D702,009 S | 4/2014 | Knapp |
| 2007/0020445 A1 | 1/2007 | Liu |
| 2007/0144698 A1 | 6/2007 | Billings |
| 2018/0271572 A1 | 9/2018 | Whyne |

OTHER PUBLICATIONS

Screen captures and YouTube video clip entitled "Triangulated 3D printed textile" 5 pages, uploaded on Aug. 16, 2017 by use r"Tomáš Vit". Retrieved from Internet: https://www.youtube.com/watch?v=Y5Wdvd9FPaE (Year: 2017).*

Tom's Fidgets ("Flippy Chain Fidget Toy Perfect for ADHD, Anxiety, and Autism-Bike Chain Fidget Stress Reducer for Adults and Kids-Blue" https://web.archive.org/web/20191018004244/https://www.amazon.com/Toms-Fidgets-Flippy-Perfect-Anxiety/dp/B01MAYBTA0/ accessed online Jun. 14, 2022 (Year: 2019).*

Screen captures and YouTube video clip entitled "3D printed fabric/chainmail" 3 pages, uploaded on Dec. 17, 2019 by user"Awesome 3DPrintz", time 3:16-4:20. Retrieved from Internet: https://www.youtube.com/watch?v=CvX368D48mU (Year: 2019).*

Tarush_Goel "Chainmail" Accessed online on Jun. 14, 2022 at https://www.thingiverse.com/thing:3491816 (Year: 2019).*

REF_1_Comments_for_Chainmail_3D Printable_Fabric_by_FLOWALISTIK_Thingiverse Accessed online on 2021.

REF_4_3D_Printed_Customized_danowall_Pinshape Accessed online on 2021.

REF_5_2_LulzBot_Posts_Facebook Accessed online 2021 Available online 2017.

REF_6_Chain_Mail_behaveslikecloth_3Dprinting Accessed online on 2021.

REF_7_251Pinterest Accessed online on 2021.

* cited by examiner

CHAIN MAIL MESH AND PROCESS FOR REDUCING STRESS

CROSS REFERENCE TO RELATED APPLICATIONS

The present application claims priority from provisional U.S. patent application 62/947,554 filed on Dec. 13, 2019, which is incorporated herein by reference in its entirety.

FIELD OF THE INVENTION

The present invention relates to a chain mail and, in particular, to a chain mail mesh configured as an anti-anxiety fidget device for reducing anxiety, fidgeting, or stress type symptoms in humans. The present invention also provides a process employing the chain mail mesh for reducing stress or inducing repeated use.

BACKGROUND

Stress and related human conditions are omnipresent and inevitable. Stress may be caused due to dissatisfaction in the workplace and personal life. The world health organization classified stress as the health epidemic of the twenty first century. Stress may lead to grave physical health and mental health issues. Physical health issues such as obesity and cardiovascular disease are on the rise. Mental health (a silent killer) has been also linked to cause physical health issues. Mental health issues such as autism spectrum, autistic, attention deficit hyperactivity disorder (ADHD), Asperger's, anxiety, nervous breakdown, and the like are also of major concern for all age groups.

Stress, whatever may be the cause, leads to a reduction in productivity at the workplace and reduces the quality of life. It is estimated that only workplace stress costs about $300 billion annually, in the United States alone, as a result of accidents, absenteeism, and similar reasons.

It is of interest to reduce stress type conditions as well as to observe their pattern. Attempts have been made in the past to develop devices and methods for reducing stress especially suited for human use. The methods include various forms of meditation, breathing exercises and the like. However, the devices and methods are somewhat unnatural and do not go a long way. This is because a person employing such devices and methods has to deliberately introduce these in his/her lifestyle and find time for the same and hence is difficult to sustain. Physical tools and toys are also known, the fidget spinner being probably the most popular.

Chain mail, also called chain mail, maille, or chain maille, was historically ring mail used for defence against physical attacks. Scale mail was used for similar purposes. Suits and other large areas of chain mail usually combined with a leather undergarment reduced cuts and spread the force of blows from mainly edged weapons. Most of these chain mail pieces were made by combining circular links made of wire formed and soldered or riveted into links connected around other links. Typical weaves include European (most commonly 4-in-1), Persian, and Japanese. Today, chain mail is still used by butchers and others for cut resistance and other physical protection. They are not sheets, other than some small pieces of such metal circular links are also used as pot scrubbers (e.g., U.S. D702,0095) that have large circular wire links that are designed to be abrasive and do not feel good against the skin. The weaves typically have more than one connection per loop where each circle connects to at least three other circles in the same open circle. Typical chain mail weaves ranged from 3-in-1 to 6-in-1, assembled in a variety of patterns. None of these weaves feel calming against the skin, likely due to significant non-planar rings, sharp edges, lack of flat surfaces, and other design elements focused on protection and ease of manufacture with primitive tools.

While not the subject of this invention, one dimensional (1-D) chains are sometimes called chain mail. These may be jewelry approximating historical chain mail elements. Classic jewelry chains, ropes and bracelets are often also made of interconnecting links, but these are very narrow and have a very high aspect ratio. These are designed mainly to bend in limited directions around a neck or wrist. Some have a large tendency to grab hair.

Typical weaves include box, byzantine, dragonscale, half Persian, helm, Jens Pind linkage, spiral rope, roundmaille, etc. Watch bands made of links also differ from the present invention in that they only bend in one direction. These bands also not usually wide enough to provide the intended interplay with the skin. Bike chains and small fidget toys made from a small number of links also differ from the present invention in that they are too small to drape over and contact enough area of skin, only bend in one direction, or do not feel sufficiently smooth.

Recently some fidget toys, stress relief toys, and puzzles, advertise themselves as chain mail or chain maille, but they have extremely limited motion. Unlike planar chain mail, these are made into tight cubes, balls, infinity roses, and other highly dense forms that like the very popular fidget spinners are designed to rotate links rather than flex them. Some weaves include Mobioius, Turkish round, etc. They are not sheets. None of these forms drape over any appreciable surface of skin and are not designed for interplay with large areas of skin.

While wire links containing a single fully open planar loop are not part of this invention, even the types of chain mail and prior uses of interconnected at least partially rigid links with high flexibility between links are not designed for the intended purpose of this invention, and while some may inadvertently approximate some of this invention's advantages, they do not maximize the targeted physiological and psychological effects induced by the use of this invention. They also generally do not minimize the negative effects of historical chain mail, including ring mail and scale mail, such as but not limited to vertical protrusions, pinching, grabbing hair, smell, skin abrasion, excessive thickness, limited drape, limited flexibility, limited range of motion, and limited contact area with the skin. Therefore, there is a need for developing simple, inexpensive ways to reduce stress at the workplace and/or in personal life.

BRIEF SUMMARY OF THE INVENTION

The present invention relates to a chain mail mesh and a process for reducing stress type symptoms or inducing repeated use of the chain mail mesh in humans or providing enjoyment by repeatedly employing the chain mail mesh disclosed herein. Stress reduction may be accomplished by the impulsive repeated playing with the swatch of the present invention.

In one aspect, the present invention provides a chain mail mesh for reducing the stress in humans and improve general feeling of wellbeing, or when humans interact with the chain mail mesh. The chain mail mesh, in accordance with the present invention, comprises a plurality of interconnecting, polygonal links suitably interconnected to define a sheet. The sheet is characterized by having a length (ML), a breadth (MB), a thickness (MT) and weight (MW), which are suitably chosen to enhance the stress reduction aspect. Each of the interconnecting, polygonal links have at least one degree of freedom of movement in at least three directions, when not at the edge of the chain mail mesh, with respect to its neighbouring polygonal links, are characterized by a length (LL), a breadth (LB), a thickness (LT), and weight (LW) and have an operative upper surface, an operative lower surface, and one or more substantially smooth edges. The operative upper surface, the operative lower surface and the one or more substantially smooth edges may have a shape selected from the group consisting of flat, concave, convex, and any combinations thereof. In an embodiment, the interconnecting, polygonal links are interconnected directly to the at least three neighbouring interconnecting, polygonal links, directly or via an intermediate connecting member. For interconnecting, polygonal links at the edge of the chain mail mesh, the interconnecting, polygonal links may only be connected to two intermediate connecting members. The term flat as used to define the contact area of the swatch, i.e., the area of the interconnected links which come into contact with the skin of a user, for example, the skin of a hand or fingers. An individual link not connected to other link is not measured because it may have side or internal corners or surfaces not intended to significantly contact the skin in the final swatch. Preferred measurement is percent external surface area of the swatch or link, as measured by the percentage of link in the outer 10% of the MT that may be felt by an adult hand when the swatch is at rest.

In one embodiment, the sheet may be rectangular or square in shape and may have about 5 to 20 interconnecting, polygonal links along the length and breadth independently and allows the swatch to drape in more than one direction.

The sheet is configured to drape when contacted with or moved over, or combinedly contacted with and moved over a human's body portion and substantially conforms to the shape of the body portion, wherein the operative lower surface of the sheet in contact with the body portion provides a calming, mood, or enjoyment effect when physically interacting with a hand or other human's body portion. The thickness (MT) of the sheet, when the sheet is in draped configuration, is different from the thickness (MT) of the sheet when the sheet is placed on a substantially flat surface, where under at rest (MT) is measured. The sheet has a predetermined drape coefficient. In an embodiment, the drape coefficient is the same along the length (ML) and the breadth (MB) of the sheet. In another embodiment, the drape coefficient is different along the length (ML) and the breadth (MB) of the sheet.

In addition to length, breadth, and thickness, an acoustic spectrum may be generated when the sheet is displaced by a user. Typically, the acoustic spectrum may comprise one or more frequencies in the range of 20 Hz to 20,000 Hz. The sheet may be tuned to a certain frequency band to provide a user with a relaxing and calming sound by suitably choosing the material of make, the dimensions, the gap, and the structure of the interconnecting, polygonal links and hence that of the sheet when in motion during typical hand play.

Further, in the chain mail mesh, the interconnecting, polygonal links are interconnected to at least three neighbouring interconnecting polygonal link, though links positioned at corner or edges of the swatch may connect to at least one, and preferably at least two, neighbouring interconnecting polygonal link, which combine to form an operative upper surface and an operative lower surface of the sheet, wherein either of the operative upper surface or the operative lower surface or preferably both are configured to contact with at least a body part of a human, and provide a calming effect thereto. More specifically, at least a portion of at least one of the operative upper surface and the exposed link surfaces in operative lower surface of the sheet generally feels smooth. The combination of this rigid pleasant surface with intermittent air gaps and nonlinear motion produce a calming or enjoyment effect when contacted with or moved over, or combinedly contacted with and moved over a human's body portion which being apt to sense of touch. The interconnecting, polygonal links within the sheet are spaced apart with a gap therebetween, which configures a loose hinge like configuration between the interconnecting, polygonal links. Further, at least a portion of the sheet which is bendable in at least one and preferably in both Z directions selected from an operative upward direction of the operative upper surface of the sheet, an operative downward direction of the operative lower surface of the sheet and a combination thereof. The gap along with the loose hinge configuration and the provision of bendability permits the sheet to drape when placed on a suitable support, very much like a piece of fabric, though in a more nonlinear mechanism of motion. In addition to the bendability, at least a portion of the sheet is skewable in at least one direction substantially parallel to a plane of the sheet. In an embodiment, the gap is in the range of 0.1 mm to 7 mm, preferably 0.3 mm to 4 mm. For example, in a 10 cm×10 cm swatch with 0.7 cm×0.7 cm links, the links are made up of connector members with an average thickness or diameter of 2 mm, a gap is 2.5 mm. The XY area of the gap is preferably less than the XY area of the solid link, as measured by percent light transmission through a swatch when the swatch is in a configuration with its smallest XY area on a light table. Due to the rigid links and constrained motion, this means that the sheet is not completely flexible and provides some resistance to drape in contrast with a typical textile fabric.

In an embodiment, the periphery of the sheet may be terminated by employing polygonal end cap links. The polygonal end cap links are connected to an outer most layer of the interconnecting, polygonal links of the sheet. The number of layers or units of the polygonal end cap links may vary. In an embodiment, the number of layers of the polygonal links may be one. In another embodiment, the number of layers of the polygonal links may be two or more. Preferably the polygonal end cap links may be the same as that of the interconnecting, polygonal links. In one embodiment, the polygonal end cap links may be different from that of the interconnecting, polygonal links, but do not materially limit the drape of the swatch. The structure of the interconnecting, polygonal links is chosen such that the operative upper surface, and/or the operative lower surface of the interconnecting, polygonal links are generally smooth to touch, thereby the operative upper surface and the operative lower surface of the sheet are also substantially smooth to touch. In an embodiment, the interconnecting, polygonal links comprises at least two lower horizontal connector members, which define the operative lower surface and at least two upper horizontal connector members, which define the operative upper surface, wherein the at least two lower horizontal connector members being connected to the at least two upper horizontal connector members at corner posts to define an incessant link.

In an embodiment, the interconnecting, polygonal links may further include at least one lower transverse intermediate connector member disposed between and connected to the at least two lower horizontal connector members and at least one upper transverse intermediate connector member disposed between and connected to the at least two upper horizontal connector members. The provision of the lower transverse intermediate connector member and upper transverse intermediate connector member further enhances the smoothness of the operative upper and the lower surfaces of the interconnecting, polygonal links and that of the sheet and at the same time provides strength to the interconnecting, polygonal links. In the preferred embodiment all members comprise the same type of link.

In accordance with the present invention, the interconnecting, polygonal links and the polygonal end cap links may be each independently manufactured from a material selected from the group consisting of plastics, elastomers, thermoplastics, composites metals, ceramics, and any combinations thereof. Plastics may comprise polymers including thermosetting polymers, UV cured resins, thermoplastics, polyolefin homopolymers, polyolefin copolymers, and the like. In an embodiment, the links may be covered with a coating covering the surface of the links. For example, the coating may be a metal coating, or a paint coating. The paint coating may be, for example, a polymer coating. The metal may include metals and metal alloys. In an embodiment the metal may be an aluminium alloy. Various non-precious metals may be coated using any suitable coating method such as, for example, electroplating. Ceramics, metal composites, ceramic composites, polymer-inorganic composites, or polymers may be metal coated or metal filled. In one embodiment, gold, titanium nitride, or silver or other decorative or protective coating may be employed.

The choice of the material depends on the drape of the sheet to be achieved, the body portion over which the sheet is used, and the weight of the sheet to be achieved. In an embodiment, the interconnecting, polygonal links and the polygonal end cap links are each manufactured from plastic in the same production machine. In an embodiment, the interconnecting, polygonal links and the polygonal end cap links are each co-dependently molded from thermoplastic.

In an embodiment, the length (ML) and the breadth (MB) of the sheet are each independently in the range of 50 mm to 250 mm, and the thickness (MT) of the sheet is in the range of 3 mm to 8 mm, when the sheet is placed on a substantially flat surface, whereas the length (LL), and the breadth (LB) of the interconnecting, polygonal links are independently in the range of 10 mm to 20 mm. In a preferred embodiment, the X:Y ratio of the sheet may be from 1:1 to 1:3, preferably approximately 1:1 for an approximated square or circle of the same area as the swatch. It is noted that X and Y, or X, Y are used herein to refer to the plane and sheet length and width of a swatch, respectively, when at rest. X is also referred to as length (ML), and Y is also referred to as breadth (MB).

In accordance with an embodiment, the interconnecting, polygonal links may have a connection form that is at least one selected from the group consisting of a three-sided polygonal link, a four-sided polygonal link, a five-sided polygonal link, and six-sided polygonal link. The preferred connection form is to have loops on three or four sides of the link in the X-Y plane. In an embodiment, the interconnecting, polygonal links, while having void spaces, may have at least one overall, approximate visual shape selected from the group consisting of a circle, triangle, a square, a rectangle, a pentagon, a hexagon, versions of these with rounded corners, and combinations thereof. In an embodiment, the interconnecting, polygonal links are square-shaped. In another embodiment, the interconnecting, polygonal links are rectangular in shape. In another embodiment, the interconnecting, polygonal links are generally cylindrical in shape with optional protrusions or pillars. In an embodiment, the interconnecting, polygonal links frame out a square shape in the X-Y plane, a flat top and bottom, same structure as the other polygonal links, and a (ML) and (MB) generally similar and in the range of 10 mm to 18 mm and (MT) in the range of 3 to 7 mm and are made of thermoplastic material.

The chain mail mesh, the interconnecting, polygonal links, and the end cap polygonal links may be each independently manufactured by any known technique including, but not limited to, 3D printing, injection molding, casting, snap fitting and combinations thereof.

In another aspect, the present invention provides a method of reducing stress or otherwise improving mental state in humans by contacting with and moving over, or combinedly contacting with and moving over a human's body portion which being apt to sense of touch, the chain mail mesh as described hereinabove, wherein the chain mail mesh intermittently contacts near nerve endings of the body portion thereby provide a calming or other positive effect thereto.

In still another aspect, the present invention provides a process for reducing stress or otherwise improving mental state in humans, the process comprising the steps, including holding the chain mail mesh, in one or both hands of a human, contacting the chain mail mesh with a body portion of the human and/or moving the chain mail mesh over the hand or other body portion of the human such that the lower operative surface and the upper operative surface contacts with nerve endings of the body portion and thereby provide a calming effect thereto, and repeating the above steps more than once to reduce the stress in humans.

The body portion is the general skin and nerve ending region, which is approximately and partially contacted with and over which the chain mail mesh is moved over time. Preferably the body portion is at least one selected from the group consisting of hand, wrist, head, forehead, shoulder, back, chest, neck, finger, calf, knee, thigh, hip, waist, foot, heel, ankle, buttock, leg, skin, and stomach and is not limited to these movement method incudes physical interaction of a subject with the swatch, and optionally visual and auditory senses. The preferred body portion is fingers and portions of the hand. Because the swatch of links provides feelable solid and air combinations and textures that at least nonlinearly change with motion, the resulting effect on the subject differs from that of typical textiles. These intermittent skin contact physical senses then lead to mental and central nervous system (CNS) effects. These resulting effects on the subject may be used to both directly affect the anxiety or other mood of the subject or as an external indicator or the subject's mood in applications such as psychological therapy, interviews, interrogation, lie detection, and the like.

BRIEF DESCRIPTION OF THE DRAWINGS

Some embodiments of the presently disclosed invention are illustrated as an example and are not limited by the figures of the accompanying drawing, wherein like references may indicate similar elements and in which.

LIST OF NUMERALS

Figure 1:
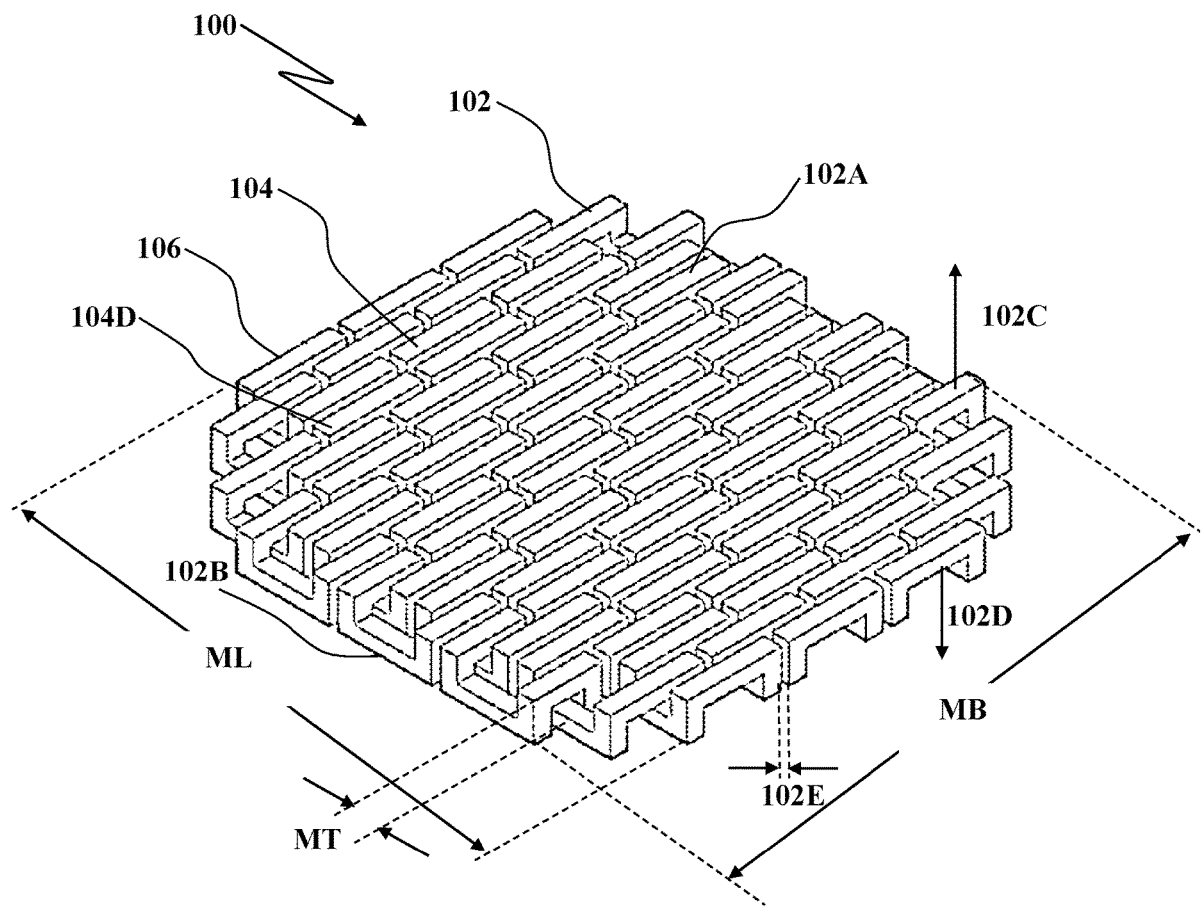
FIG. 1 illustrates an isometric view of a chain mail mesh of the presently disclosed invention, wherein the chain mail mesh is in the form of a sheet, with square end cap links and with identical square-shaped interconnecting, polygonal links.

100—Chain mail mesh
102—Sheet
102A—Operative upper surface of the sheet 102
102B—Operative lower surface of the sheet 102
102C—Operative upward direction
102D—Operative downward direction
102E—Gap between two interconnecting, polygonal links
104—Interconnecting, polygonal links
104A—Operative upper surface of the interconnecting, polygonal links
104B—Operative lower surface of the interconnecting, polygonal links
104C—Smooth edges
104D—Outermost layer of the interconnecting, polygonal links 104
1042—Lower horizontal connector member (first)
1044—Lower horizontal connector member (second)
1046—Upper horizontal connector member (first)
1048—Upper horizontal connector member (second)
1050—Corner posts
1052—Lower transverse intermediate connector member
1054—Upper transverse intermediate connector member
106—polygonal end cap links
ML—Length of the sheet 102
MB—Breadth of the sheet 102
MT—Thickness of the sheet 102
LL—Length of the interconnecting polygonal link 104
LB—Breadth of the interconnecting polygonal link 104

LIST OF VARIABLES

I—Length (ML) of the sheet 102
II—Breadth (MB) of the sheet 102
III—Thickness (MT) of the sheet 102
IV—Length (LL) of the interconnecting polygonal link 104
V—Breadth (LB) of the interconnecting polygonal link 104
VI—Thickness (LT) of the interconnecting polygonal link 104
VII—Colour of the sheet 102
VIII—Colour of the interconnecting, polygonal links 104
IX—Colour of the polygonal end cap link 106
X—Material of make of the interconnecting polygonal link 104
XI—Material of make of the polygonal end cap link 106
XII—Gap (102E) between two interconnecting, polygonal links 104
XIII—Drape coefficient of the sheet 102
XIV—Radius of curvature of the sheet 102
XV—Weight (MW) of the sheet 102
XVI—Weight (LW) of the interconnecting, polygonal links 104
XVII—Number of sides of the interconnecting, polygonal links 104
XVIII—Shape of the interconnecting, polygonal links 104
XIX—Number of sides of the polygonal end cap link 106
XX—Shape of the polygonal end cap link 106
XXI—Acoustic spectrum frequency band emitted by the chain mail mesh 100
XXII—Operative upper or operative lower surface area of the sheet 102
XXIII—Operative upper or operative lower surface area of the interconnecting, polygonal links 104
XXIV Length of the intermediate connecting member
XXV Breadth of the intermediate connecting member
XXVI Thickness of the intermediate connecting member
XXVII Weight of the intermediate connecting member
XXVIII Material of make of the intermediate connecting member
XXIX Shape of the intermediate connecting member

DETAILED DESCRIPTION OF THE INVENTION

All technical terms and scientific expressions used in the present invention have the same meaning as understood by a person skilled in the art to which the present invention belongs, unless and otherwise specified. As used in the present specification and the claims, the singular forms "a", "an" and "the" include plural references unless the context clearly dictates otherwise.

The term "comprising" as used in the present specification and the claims may be understood to mean that the list following is non-exhaustive and may or may not include any other extra suitable things, for instance, one or more additional feature(s), part(s) and/or constituent(s) as applicable.

Further, the terms "about" and "approximately" used in combination with ranges of sizes of parts, particles, compositions of mixtures, and/or any other physical properties or characteristics, are meant to include small variations that may occur in the upper and/or lower limits of the ranges of sizes.

Swatch or Chain mail or chain mail mesh is defined herein to mean a fabric of interconnecting rigid links, wherein the links are large enough to be individually felt by human fingers or any body parts and their connection flexible and loose enough to drape the fabric over a body part of a human, for example, a hand of a human.

Rigid link means the link has a stiffness or flexural modulus of at least 1.5 GPa, as measured by ASTM D790 and ISO 178 bend test method.

Stress as this term is employed herein may also include other human conditions, symptoms, and manifestations of mind, body or both that cause a human to feel less than happy.

Smooth surface or edge refers to the texture of a surface or edge which feels generally smooth to the human touch and is substantially free of sharp edges or profiles.

Loose hinge or loose loop as used herein means a coupling or a connection between two adjacent interconnecting, polygonal links and/or an interconnecting polygonal link and a polygonal end cap link and/or between an interconnecting polygonal link and an intermediate connecting member, wherein the coupling or connection is similar to a hinge in allowing constrained motion, but is loose thereby enabling relatively free movement of the interconnecting, polygonal links, polygonal end cap links and intermediate connecting member as compared to conventional hinges. Free movement means both looseness or rattle, and movement outside of the single rotational direction. Loop is a functional description of this loose connection means. As a hinge has loops and a pin, the links have constraining closed loops or partially constrained loop sections that constrain loops of portions of neighbouring interconnecting, polygonal links. A loop may also comprise integral structural parts of the interconnecting, polygonal links.

Neighbouring interconnecting, polygonal links may include an immediate neighbouring interconnecting polygonal link or may also include a connecting link between such interconnecting polygonal links.

Skewable as this term is used herein means that the sheet and/or the chain mail mesh may be at least slightly distorted at least either lengthwise or breadthwise or both by moving the interconnecting, polygonal links and/or the polygonal end cap links and/or the intermediate connecting members.

The at rest state or XY area of the swatch refers to the area defined by the swatch perimeter in the X-Y plane when the swatch is placed on a flat, hard surface on the X-Y plane, gently pulled out to its maximum area, and released to rest on the flat, hard surface.

Link looseness refers to the play between the loop and the adjoining link. For example, loops have at least one inner dimension that is larger than the connecting link part in that loop to allow some play in the motion between the link with the loop and the connecting link. This play may often allow features such as fast motion, looseness in motion, noise of rattles or jangles, as compared to a limited motion device such as a door hinge.

Resistance to motion may limit the motion of the neighbouring links and of the swatch in aspects such as direction of motion, limit of motion, speed, acceleration, friction, and the like. It is mainly controlled by link location, link shape, link looseness, and collision between adjacent link may constrain maximum range motion.

Drapability also referred to herein as drape is the ability of the swatch to significantly flex such that at least a majority of the XY edges of a swatch to bend at least 65 degrees from the X-Y plane when placed on a circle with a diameter at least 1.5 times that of the average diameter of the largest link in that swatch. While not optimal for composite nonlinear materials, this may be measured by a Drapemeter under the British standard for the assessment of drape of fabrics (BS 5058) where the ratio of the projected area of the chain mail mesh to its undraped area, in which the area of a supporting disk is deduced. The sample may be the swatch rather than the small sample the standard uses for typical textile fabric. Preferably, the unsupported area may drape to form some at least partial folds. The number of the folds (nodes) is used to describe the drapability directly. The more the nodes, the softer is the fabric. The drape coefficient is the ratio of the projected area of the fabric sample to its undraped area, in which the area of the supporting disk is deduced. High drape is desired unlike chain mail and other armor where high drape reduces physical protection.

The drape coefficient of composite textiles is generally more difficult to measure than traditional textiles. An objective method for the determination of fabric samples mechanical properties is known as the "jutting strip method" or "cantilever method" which has been developed by Pierce in 1930 and is included in the FAST system (Fabric Assurance by Simply Testing). The bending property, making a part of the overall mechanical characterization of the swatch may be correlated to a drapability. See, Smart Textiles for In Situ Monitoring of Composites, Vladan Koncar, Woodhead Publishing, Oct. 29, 2018—Technology & Engineering, p. 218. For simplicity, this invention measures both drape and drape coefficient as the minimum deflection in the Z direction of a swatch in the X-Y plane. A plastic swatch may have a smaller radius of drape, where drape will not substantially differ over a wire, or measurement circle of up to 0.5 cm because it typically will have larger links. A metal swatch due to mechanical strength can have smaller links and smaller connecting means than plastic and, therefore, would have a larger drape because while still a composite, it can move in a manner closer to that of a traditional non-composite textile. The inventive swatch may be able to both generally lay flat on a flat hard surface and roughly drape over a 3D shape such as a hand or ball, though the link size and swatch flexibility may usually not touch the entire 3D shape.

The present invention uses a sheet of flexible links, herein defined as a swatch. While the applicant uses the term chain mail, the current invention does not use traditional ring mail weaves of wire or sharp-edged loops or large protective garments. Rather the links and the swatch are designed to provide several important physical attributes to maximize enjoyment or satisfaction of a user playing with that swatch.

The swatch of this invention has a very particular type of segmented motion due to link spacing and connection means, unlike a completely flexible cloth or thin silicone elastomer sheet. The direction of motion is constrained in that the swatch bends in more than one direction, but by a nonlinear method. The motion is not necessarily simultaneous in all directions or linear at all swatch conformations. For example, the swatch may simultaneously bend in multiple directions to increase hand contact and variety of contact.

The term swatch as used in this disclosure refers to the chain mail sheet that comprises the links and has the size, and flexibility designed to impart the psychological and physiological effect on the user. It is predominantly defined by X (ML), Y (MB) and Z (MT) dimensions, but to maximize intended psychological benefits, also requires specific combinations of ranges of link size, flatness, weight, flexibility and mode of motion. Flexibility is defined as the ability to bend without excessive force such that at least three non-adjoining links can touch.

When placed on a flat hard surface, on the X-Y plane, gently pulled out to its maximum area, and then released, the swatch is herein defined to be in its at rest state, and comprises at least a majority and preferably all or almost all of the following attributes:

A) The general swatch shape may have an aspect ratio no greater than an equilateral triangle or otherwise approximate no more than a 1:4 X:Y ratio, preferably less than a 1:1.33 X:Y ratio. In the Z direction, the shape should give the swatch a look of a roughly approximate sheet when at rest with the totality of the links, not counting voids, averaging two parallel surfaces that encompass the operative upper surface and the operative lower surfaces. In an embodiment the two parallel surfaces may differ.

In an embodiment the swatch may approximate in the X-Y plane the shape of a circle, ellipse, triangle, rectangle, square, rectangle, pentagon, hexagon, octagon, or any combinations thereof. In a preferred embodiment, the swatch shape in the X-Y plane may be a square or a square with missing corner pieces. In another embodiment the swatch shape in the X-Y plane may be an ellipse. In a particular embodiment the swatch shape in the X-Y plane may be a circle.

B) The shape of the link is mainly limited by the loop or other connection means location to determine direction of bend and how the shape of the link and the loop constrain the direction and extent of motion with the adjacent links and therefore the overall swatch. In an embodiment shape may be determined by performance to cost, manufacturing, packaging or aesthetics.

C) The swatch's shape when taken to approximate an ellipse or rectangle may have an X-Y aspect ratio within 1:1 to 1:4.

D) When at an at rest state, the swatch X-Y area may be from 10 $cm^2$ to 1,000 $cm^2$, preferably from 20 $cm^2$ to 500 $cm^2$, more preferably from 15 $cm^2$ to 500 $cm^2$, and most preferably from 25 $cm^2$ to 400 $cm^2$. In an embodiment, the swatch may approximate a square or square with chamfered corners with a length and width within the range of 6 cm to 10 cm. In another embodiment, the swatch may approximate a circle with a diameter from 3 cm to 10 cm.

E) The swatch may be highly flexible. In an embodiment at least one edge of the swatch sheet should be able to touch the opposite XY side of the swatch when the swatch is freely bent, in its two most flexible directions, over a rigid rod with a diameter of less than 3 mm.

F) The swatch may bend in multiple directions so that it has sufficient drape that it may at least loosely drape over at least one of a Reuleaux tetrahedron, rounded tetrahedron, ellipsoid or hemisphere with a maximum diameter or edge of 5 cm and surface area of less than the swatch XY area. In one embodiment the swatch may be easily crumpled in three dimensions to change from a X-Y sheet to a 3D structure with a Z dimension of at least 3 times that of the sheet's MT.

G) The swatch may be sufficiently loose such that it may bend under its own weight.

H) The swatch may have some give. By give as this term is used here we mean that the width of the gaps formed at the top operative surface or at the bottom operative surface may be increased or reduced by the user because the interconnecting links are loosely connected allowing a link to move in the X or Y direction relative to its neighbouring link. This movement or give in the X-Y plane may result, for example, that the preferred minimum X-Y area may be within 70% to 96% of the at rest area. The at rest area is also referred to herein as a maximum area.

I) The swatch may comprise flat or approximately flat external surfaces available to touch.

J) The swatch should not have uncomfortably sharp edges or sharp protrusions.

The swatch thickness (MT) is within 1 mm to 10 mm and preferably within 2 mm to 7 mm. The thickness of the swatch (MT) may be sufficiently large for preventing formation of sharp surfaces and for allowing human touching and perception of individual links, but not so large as to impede the intended motion, looseness, and drape of the swatch. A preferred thickness may partially be dependent on the material weight and strength. For example, a stronger material, e.g., metal, may provide the required strength for thinner walled loops and, therefore, thinner swatches.

The swatch may be made of at least one type of link, meaning that all the links are of the same shape and size. However, more than one type of links may be used. In an embodiment 2-3 types of links may be used. In a preferred embodiment one type of link is used.

In an embodiment, the swatch may have a polygon such as a triangle, a square etc, with a plurality of swatch's corners. In another embodiment, the corners may be eliminated because from an operational perspective they may be too sharp, droopy, loose, or unconstrained.

Each link in the swatch, other than optionally corner links, may be connected to at least three other links. In a preferred embodiment, each corner and edge link may be flexibly connected to 2-4 other links, and each other link may be flexibly connected to 3-6 other links, and preferably to 3-4 other links. The preferred embodiment has 3 or 4 connection means per link generally forming a triangle or square from the flexible connection perspective, while visually the link may approximate other shapes described herein.

In an embodiment, additional links with different flexibility or lack thereof that may provide additional functionality such as LED light, sound, color, and the like, may be employed in addition to the flexible links. Preferably, link types may be less than 9, more preferably less than 5, and most preferably less than 2.

The swatch may have an overall macro roughness that is greater than that of a woven textile fabric but significantly less than a traditional ring chain mail mesh. In other words the swatch may have an overall macro smoothness that is less than that of a woven textile fabric but significantly more than a traditional ring chain mail mesh. The present invention achieves this by employing generally flat external surfaces and a sufficiently large ratio of touch surfaces to the total area covered by the swatch. These touch surfaces combined with a smaller percentage of void space are present in both in a flat X-Y sheet form as well other conformal forms of the swatch.

The swatch may have a flatness wherein 5-90%, preferably 20-90%, more preferably 40-90% and most preferably 60-90% of the touchable surface (also referred to as the contact area of the swatch) of the top side and optionally the top and bottom side is flat. The contact area of the swatch is the area of the interconnected links which come into contact with the skin of a user, for example, the skin of a hand or fingers. An individual link not connected to other link is not measured because it may have side or internal corners or surfaces not intended to significantly contact the skin in the final swatch.

The swatch may have a sufficient solid coverage such that when the swatch rests on a flat surface and in smallest contracted size without continuous external applied force, at least some portion of the swatch covers 20% of the X-Y plane, preferably, at least 25%, and, more preferably, at least 33% of the X-Y plane. This coverage is best measured by placing the swatch at rest on a flat light table and measuring the reduction in transmitted light. Ring mail and other link forms with large extremities but small material cross-section may not provide this coverage.

The volumetric density (in XYZ space) may affect important aspects of the swatch and its use such as but not limited to weight, feel, and looseness. Volumetric density may also be used as a method to measure such properties, but is defined to describe the general swatch and not the link material or material porosity within the link. For a swatch made of plastic interconnecting links, the preferred volumetric density when contracted or at rest, is 20 to 50 vol % and preferably 30-40 vol %. Some designs that do not stretch significantly in the XY plane, may require more volumetric stretch to ensure sufficient flexiblity.

The swatch may preferably consist of one layer of links, though some embodiments may have 1-3 layers of chain or a combination of main links and loose, highly flexible connecting means such as loops, thread, fiber, fabric or sheet included in these layers.

The swatch may have an aesthetic look that includes at least one of a colour, a surface printing, a coating, a painting, and a pattern of coloured links. Some of these treatments such as coating may be multifunctional, e.g., also affect feel and motion.

The swatch may not have rigid frames that impede intended flexibility and drape. The swatch may optionally have differing edge links. The swatch may, for example, be generally uniformly flexible along the swatch, with the same type of link or links throughout the swatch, though such links on the edge may naturally have less support from other links and may be more pendent. Although different types of interconnecting links may be used, a preferred link may have sufficient complexity and volumetric coverage. A preferred link may not be a simple circle or loop. A preferred link may have at least twice the contact with a flat surface than does a chain mail made of wire loops.

The links are the discrete parts that make up the swatch and also have very specific requirements in order to impart or maximize the beneficial interactions with the user during intended use of this invention.

The maximum dimensions of a link are X or length (LL), Y or, a breadth (LB), and Z or a thickness (LT). The size partially depends on the material. For plastic, the preferred LL and LB are within 0.3 cm to 2.5 cm. For a square, rectangle, or version thereof without corner links, the preferred LL and LB are within 1.1 cm to 1.5 cm. For triangular, LL (base) and LB (base to apex) are within 1 cm to 2 cm, and preferably within 1.2 cm to 1.7 cm. Large links, e.g., links having sides >2 cm are not preferred.

The thickness Z or (LT) defines overall maximum thickness (Z) between upper surface, and lower operative surfaces. LT is proportionate to weight. For plastic LT may be within 3.5 mm to 20 mm, and preferably within 4 mm to 10 mm. For metal LT may be within 0.5 mm to 10 mm, and preferably may be within 0.6 mm to 7 mm. An embodiment has an LT of 3-4 mm. LT may not be too thick or it may not feel as pleasant and often may interfere with flex and drape.

The movement area is defined in the Z direction as LT minus the maximum link thickness or diameter in any XYZ direction of the top minus the maximum link thickness or diameter in any XYZ direction of the bottom v during motion (e.g., a rectangular cross-section may be thickest at 45 degrees). This movement area must allow free motion of the swatch in the intended directions and intended range of motion, though it may create friction, otherwise slow, or stop motion in other directions depending on the swatch conformation at the time.

The link may have a shape which approximates in the X-Y plane a circle, an ellipse, a triangle, a rectangle, a square, a pentagon, an hexagon or an octagon. The link may have a shape having an X:Y or ML:MB aspect ratio no greater than 1:2, preferably less than a 1:1.33. While it is rather easy to measure for a rectangle or ellipse, other shapes such as an equilateral triangle for example would also fall within this ratio. In the Z direction, the shape of the link may provide significant smooth feeling surface to the touch. The top and bottom surfaces of the link may be identical in terms of smoothness, shape, and size, although their orientation may differ as, it is shown, for example in the embodiment of FIG. 2C. However, in other embodiments, the top and bottom surfaces of the link may differ not only in orientation but, also, in at least one of smoothness, shape, and size. For example, in an embodiment the bottom surfaces of the link may be substantially flat while the top surfaces may include a flat portion and a curved portion. Preferably, the shape of the link from a top or bottom view (i.e., in the XY plane) may be a square, a triangle, or a modified square or triangle having their corners smoothed out. Link shapes that are pentagons, or hexagons are less preferred because of the larger number of connection means required which increase the complexity of the design. The connection means may preferably be 3 or 4 per link. The link may be formed to include a plurality of at least one of the following types of elongated elements including beams or rods having a circular, oval, or rectangular cross section. For example, the elongated elements may include a straight cylinder, a bend cylinder, a straight beam, a bend beam, a twisted cylinder, a twisted beam pillars, and other rods that are configured to provide the desired general shape of the link and have at least a portion thereof being flat or substantially flat surface in the XY plane. For example, in an embodiment, the elongated element may have an XY plane surface that is a combination of a flat and a curved surface. In an embodiment, the link may have a Cuban chain link shape significantly modified to connect and flex in a 2-D sheet. In a preferred embodiment, the swatch is a square or a square with missing corner pieces. The shape of the link may also be a square or a square with missing corner pieces. The shape of the link is mainly limited by the loop location that determines bend direction and how the shape of the link and the loop constrain the direction and extent of motion with the adjacent links and therefore the overall swatch. In an embodiment the loop is the link. Sharp corners are also to be rounded or minimized when they may provide an uncomfortable sensation by the user.

A Loop is the part of the link that holds an adjoining link and allows generally free motion of that adjoining link in a constrained direction. A link may be merely the space between posts. A loop is defined as the physical or functional method of loosely coupling links. Rigid hinges are not contemplated. Single wire loops or other similar single simple circles or ovals without significant contortion and wall thickness are not contemplated other than in swatches with at least two link types where the circle serves as a connecting link, and that connecting link is generally shielded from the skin in most swatch configurations by the other type, non-circle links. More complex link shapes may contain circle or loop elements such as two at least partially flattened circles connected by posts or loops. A loop may be combination (e.g., pillars in center, loops on outside to retain "smooth" feel during motion. Loops may be at least partially coated to modify feel or to apply friction to motion. For example, there may be only one connection per loop, though the loop may be defined by position or other constraints to motion than a completely closed loop. Concave Curb Cuban link chain and Miami Cuban Link Chain are one-dimensional examples incorporating such a link that contains only one opening but functionally defines three loops. The walls, pillars, freeform enclosure, or other link parts defining the loop may be strong enough to withstand repeated play without application of force beyond the swatch weight.

All or a majority of the X-Y plane areas of the links may have a flat or substantially flat portion of their externally facing surface area of the link's external upper surface and lower surface. Substantially flat includes small deviations from flat due to manufacturing limitations, intentional inclusion of edge chamfer or fillet, and intentional inclusion of smooth protrusions that impart roughness. In a preferred embodiment, both the top side and the bottom side have identical flat or substantially flat surfaces. In an embodiment one of the top or bottom sides comprise non-overlapping plates sufficiently separated to allow the intended range of motion in at least one Z direction.

The links may preferably be rigid. For example, rigid links made of a polymer material such as a thermoset or thermoplastic material or metal may be used for the swatch. The links may be coated with a metal or polymer coating. For example, the coating may be an elastomeric or a coloured coating.

Higher weight and therefore higher density of links are preferred. Links may be solid or have a porosity of less than 50 vol % as compared to the solid coverage of the swatch. Higher density is preferred within a range of from 0.5 g/cm$^3$ to 10 g/cm$^3$, 0.8 g/cm$^3$ to 1.55 g/cm$^3$ for plastic, 2.5 g/cm$^3$ to 8 g/cm$^3$ for metal, and 1 g/cm$^3$ to 8 g/cm$^3$ for composite or coated links such as, for example, metal coated metal or plastic, plastic or metal coated metal. The preferred mode uses an inexpensive, easily manufacturable material such as a plastic material or cast metal, e.g., plated or coated zinc casting.

The links may not have any sharp external edges that would be touchable in normal swatch conformations and draped forms. Any touchable edges may be preferably rounded, with a chamfer, fillet, coating or other softening or removal technique. This does not mean that the swatch may be completely smooth. The interplay between hard surfaces and spaces in between in a range of 3D motion is necessary for this present invention's use. In a preferred embodiment, the links are rounded with flat or substantially flat profile on both external XY plane surfaces. The inside part of the link that is not normally touchable is not important as far as roughness, sharpness and finish other than in how it adversely affects rate of motion or noise of the swatch.

The operative upper (top) surface and operative lower (bottom) surface are connected by vertical connections between top layer and bottom layer. The number of posts or other such connections may vary between 3 and 8, preferably between 3 and 7, and more preferably either 5-7 or 3-6. The posts may have varied forms such as but not limited to pillar, curved, loops, free forms connecting top and bottom. Links may have a mix of posts, angled posts, and other types of vertical connections (e.g., curved). In an embodiment there are no posts and a thread or fiber may connect the links. In an embodiment links may also comprise or simply contain one or more highly bent loops.

The terms such as flat and substantially flat surface, includes completely flat and approximately flat surfaces, which are not completely flat. An operative upper surface and operative lower surface includes surfaces that are or appear to be upper and lower respectively when in use.

Figure 2A:
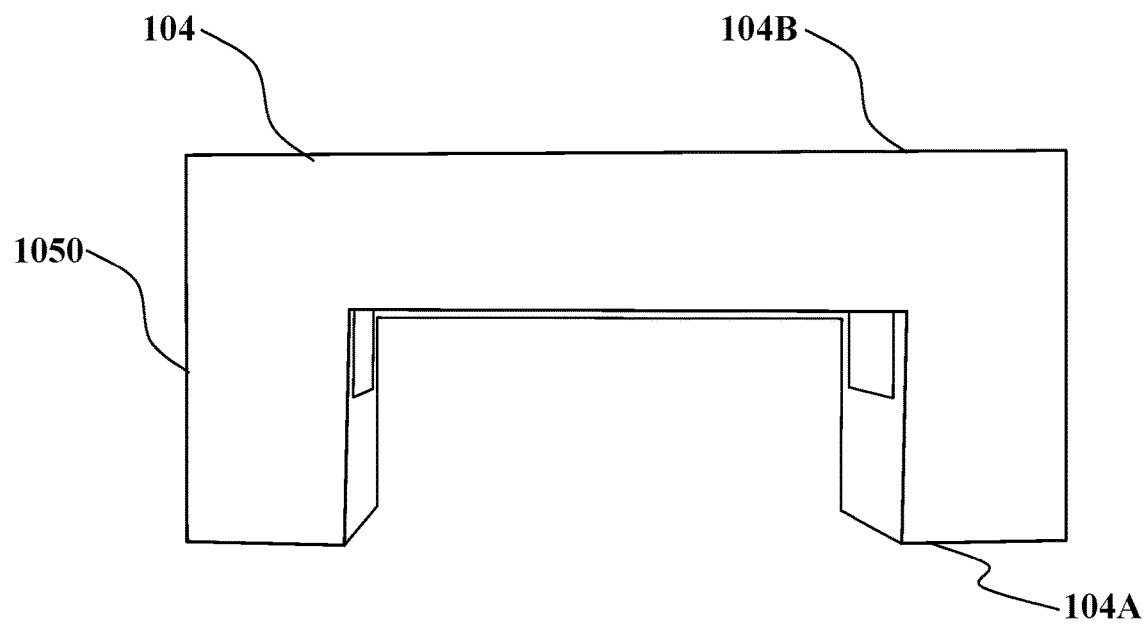
FIG. 2A illustrates a side view of an interconnecting polygonal link in accordance with an embodiment of the present invention.
Figure 2B:
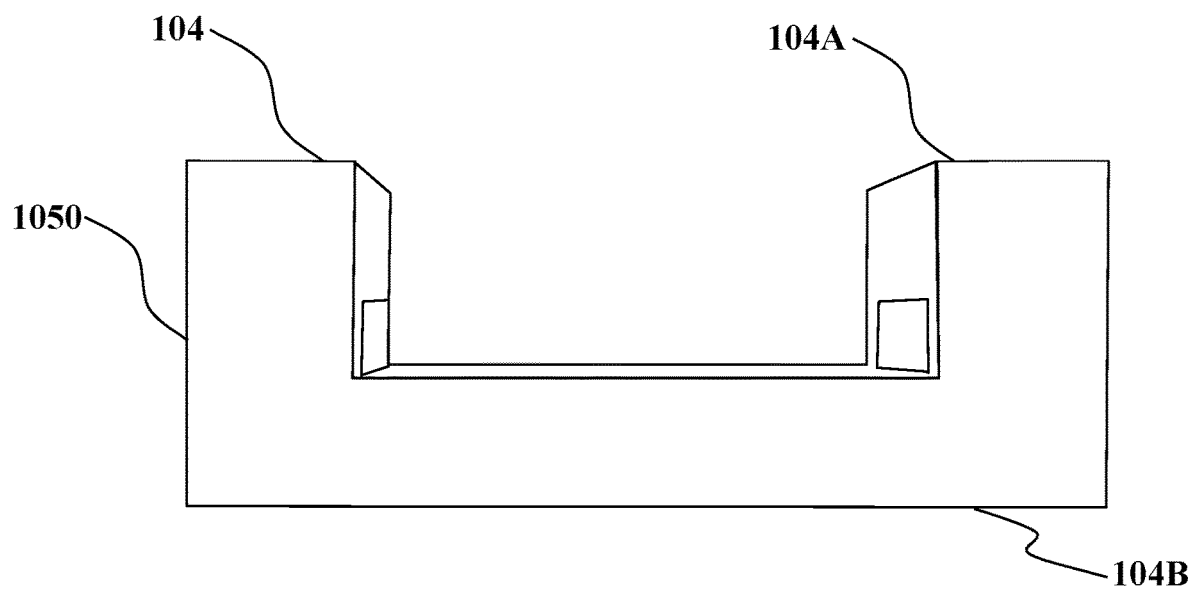
FIG. 2B illustrates another side view of the interconnecting polygonal link of FIG. 2A.
Figure 2C:
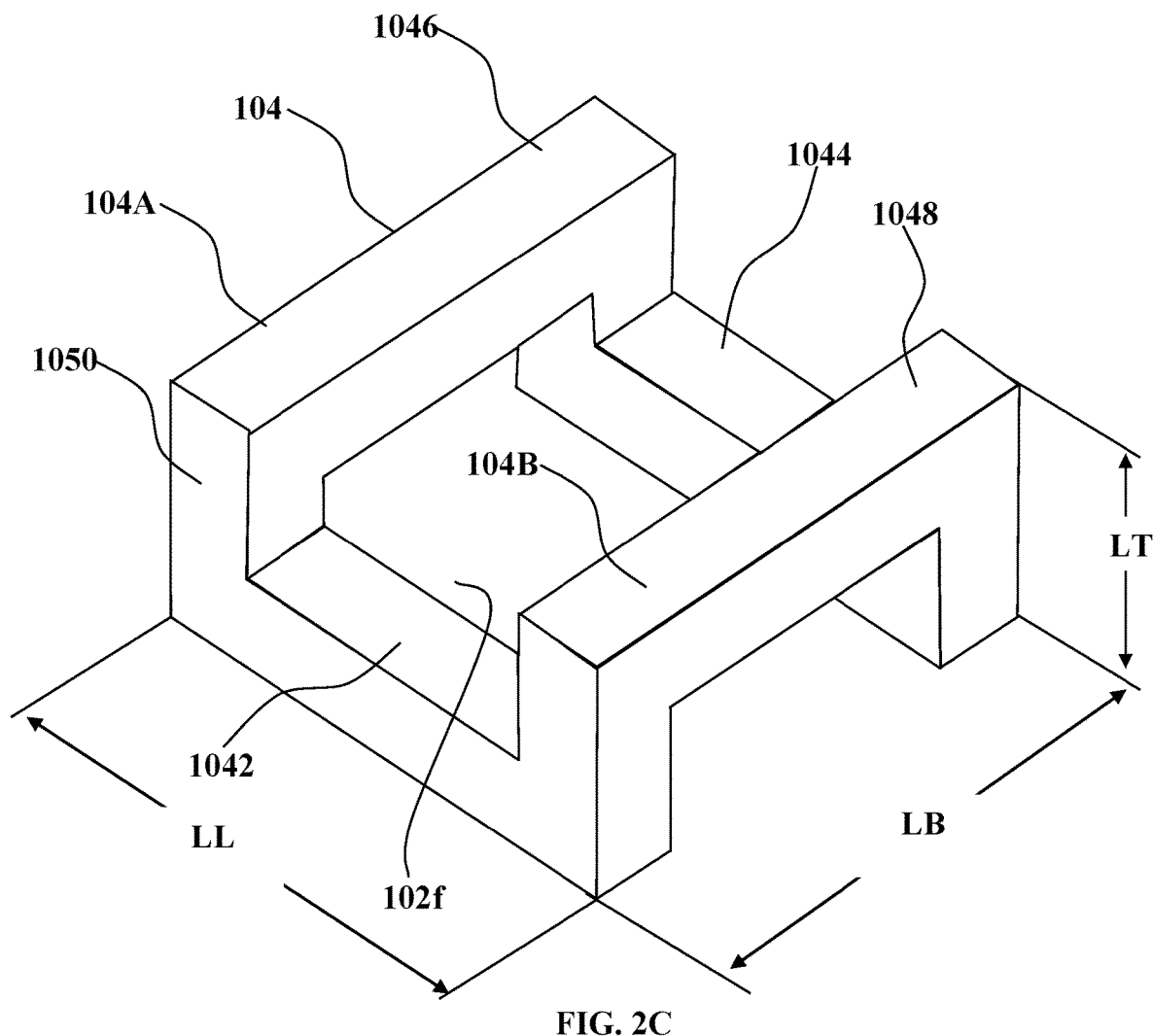
FIG. 2C illustrates a perspective view of the interconnecting polygonal link of FIG. 2A.
Figure 3A:
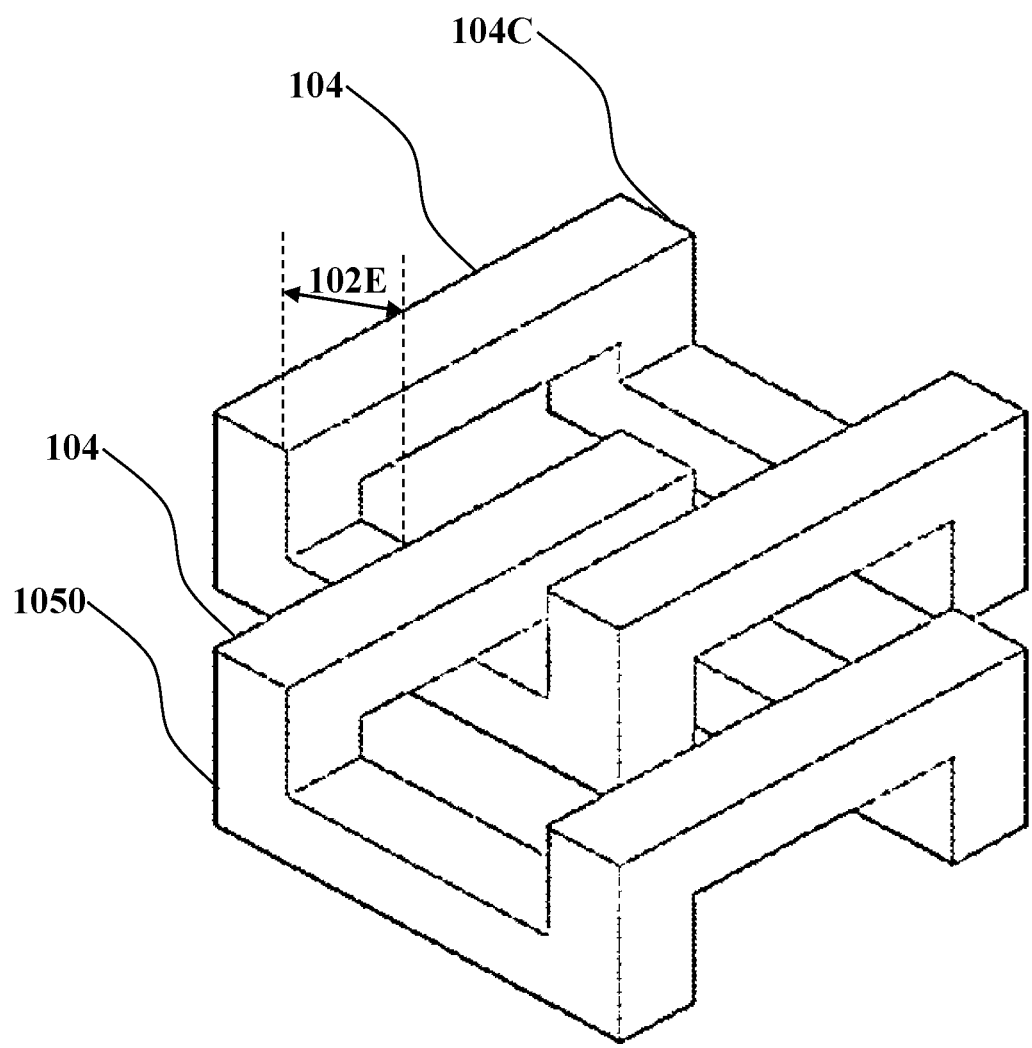
FIG. 3A illustrates a perspective view of a pair of interconnecting, polygonal links of FIG. 2A, wherein two interconnecting, polygonal links (having a square shape) are connected together.
Figure 3B:
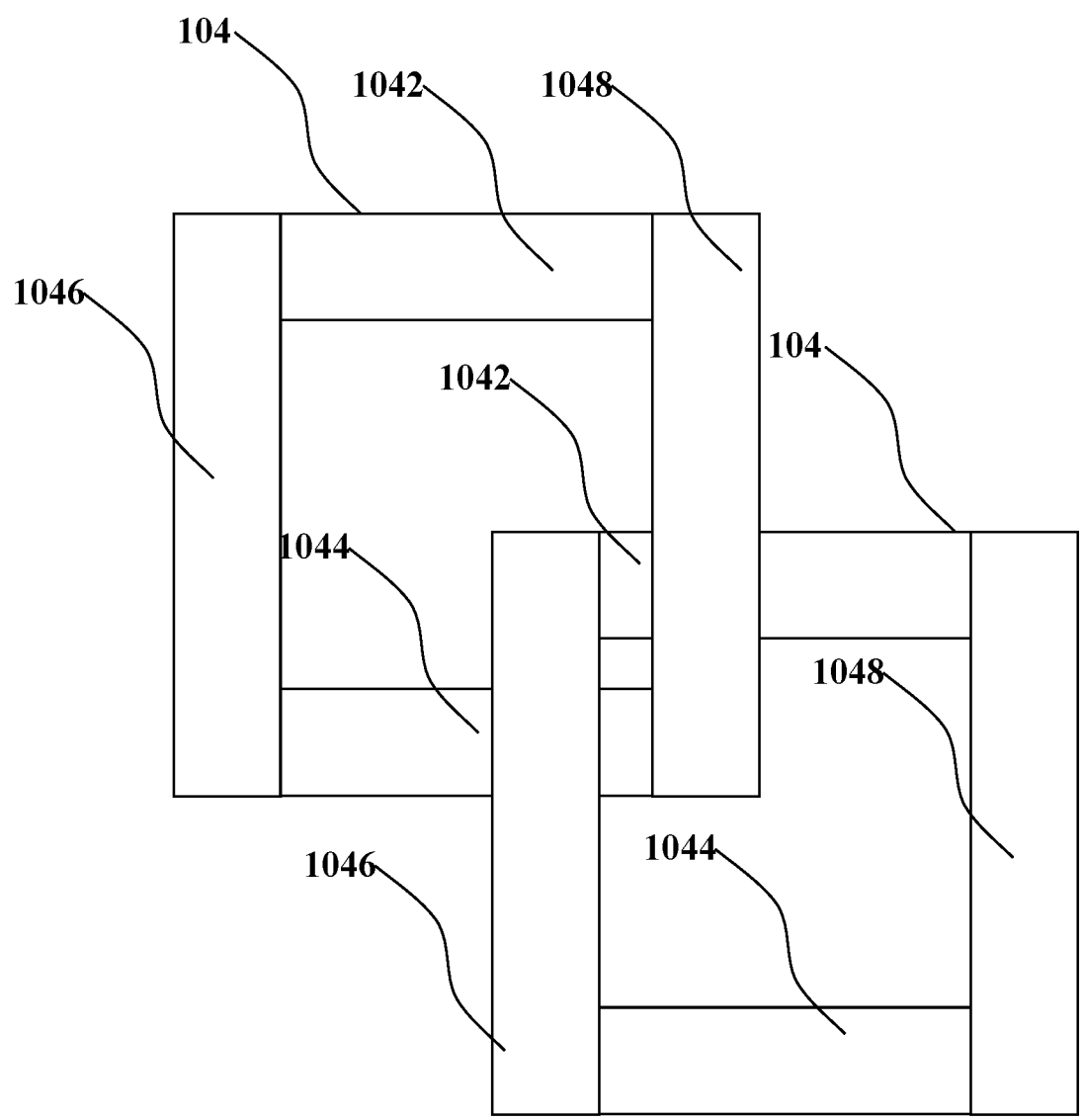
FIG. 3B illustrates a top view of the pair of the interconnecting, polygonal links of FIG. 3A.
Figure 4A:
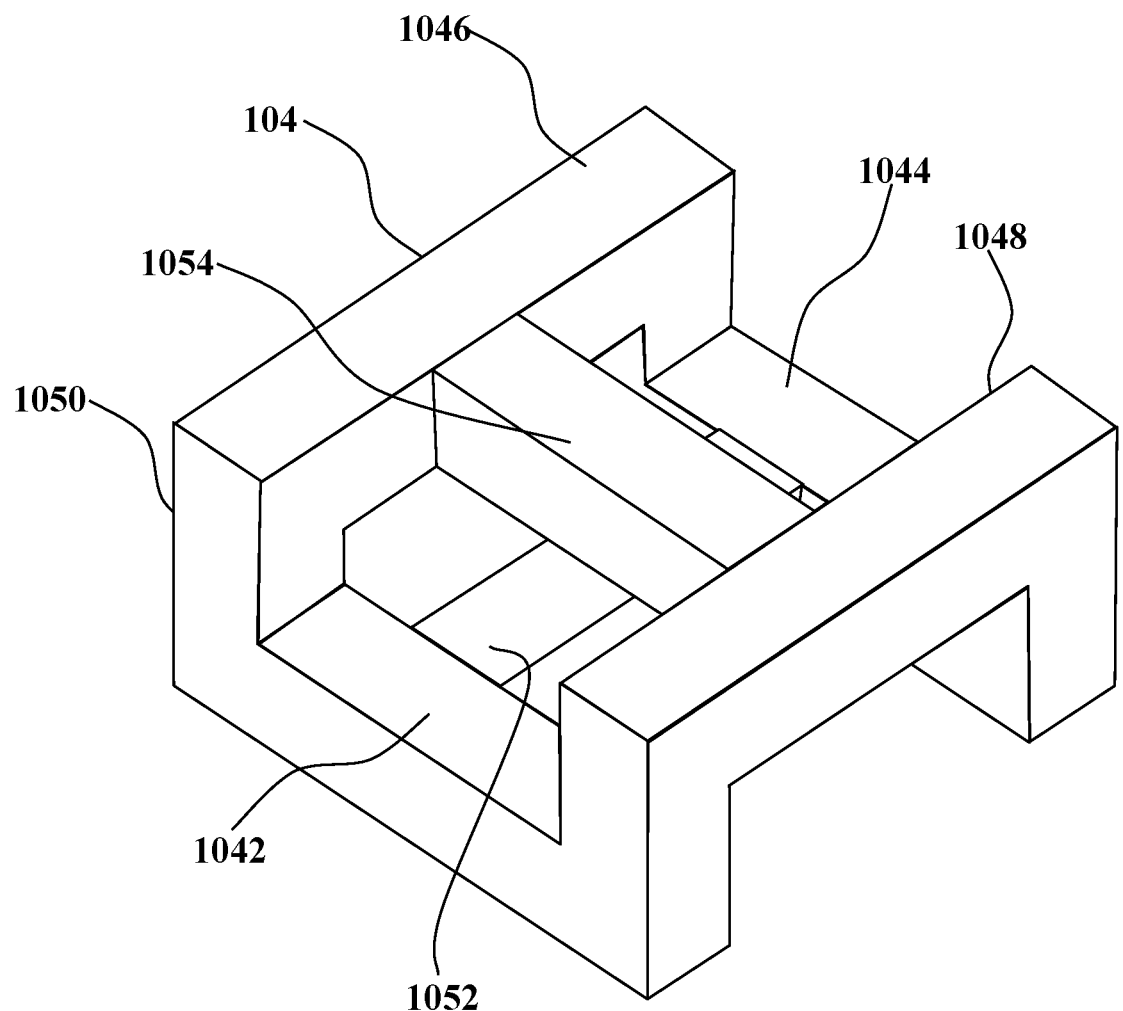
FIG. 4A illustrates an isometric view of an interconnecting polygonal link in accordance with another embodiment of the present invention.
Figure 4B:
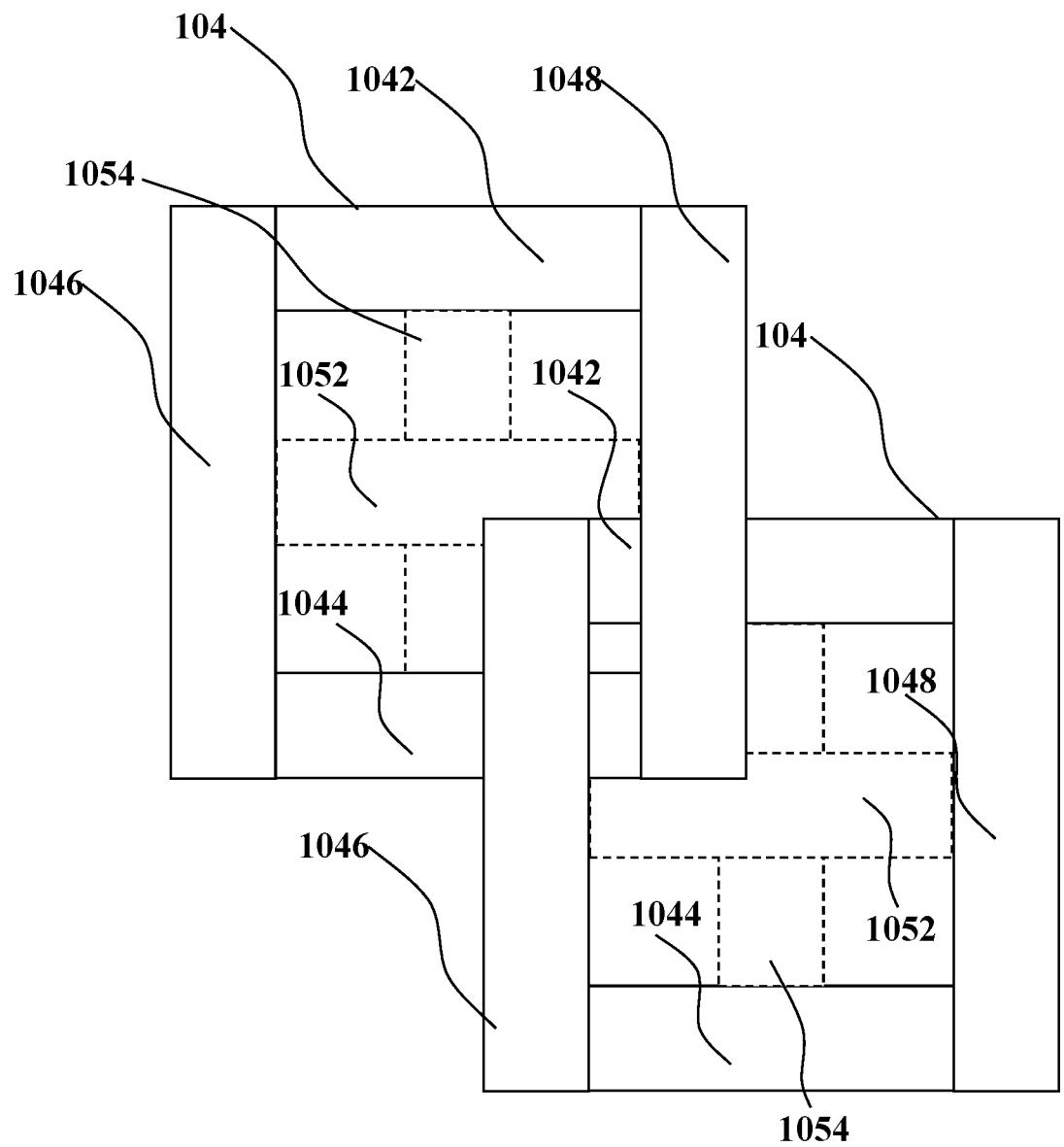
FIG. 4B illustrates a top view of a pair of interconnecting, polygonal links of FIG. 4A, wherein two interconnecting, polygonal links (having a square shape) are connected together.

The present invention is now described hereinbelow with reference to the accompanying drawings, wherein FIG. 1 illustrates an isometric view of a chain mail mesh of the presently disclosed invention, wherein the chain mail mesh is in the form of a sheet, with square end cap links and with identical square-shaped interconnecting, polygonal links, FIG. 2A illustrates a side view of an interconnecting polygonal link in accordance with an embodiment of the present invention, FIG. 2B illustrates another side view of the interconnecting polygonal link of FIG. 2A, FIG. 2C illustrates a perspective view of the interconnecting polygonal link of FIG. 2A, FIG. 3A illustrates a perspective view of a pair of interconnecting, polygonal links of FIG. 2A, wherein two interconnecting, polygonal links (having a square shape) are connected together, FIG. 3B illustrates a top view of the pair of interconnecting, polygonal links of FIG. 3A, FIG. 4A illustrates an isometric view of an interconnecting polygonal link in accordance with another embodiment of the present invention, and FIG. 4B illustrates a top view of a pair of interconnecting, polygonal links of FIG. 4A, wherein two interconnecting, polygonal links (having a square shape) are connected together.

Figure 5:
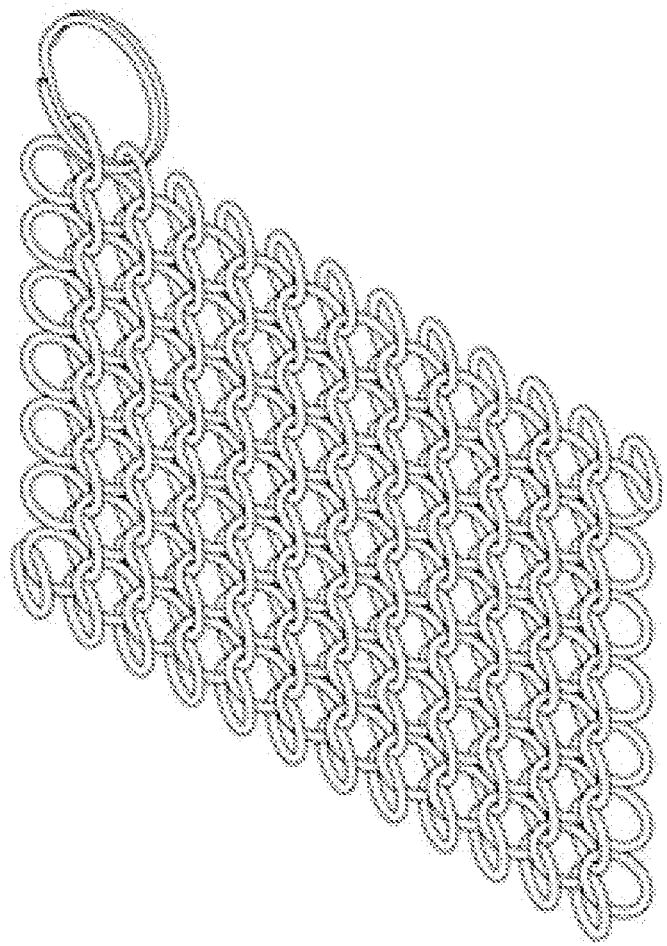
FIG. 5 illustrates a conventional chain mail mesh having ring-shaped interconnecting links and made of metal.

The present invention provides a chain mail mesh 100 which when employed by a human suitably, leads to a significant reduction in stress. Typically, the chain mail mesh 100, when contacted with and/or moved over a body part (such as, for example the skin of the top part of a hand) of the human provides a soothing effect to the body part. Also, the chain mail mesh 100 functions as an anti-fidgeting device that engages the attention of a human and releases its anxiety and stress by the repeated use of the chain mail mesh. The chain mail mesh 100 (FIG. 1) of the present invention is different from those encountered in the prior art. For example, FIG. 5 illustrates a conventional chain mail mesh having ring-shaped interconnecting links and made of metal. The conventional chain mail mesh of FIG. 5 has a very bumpy surface and is not at all smooth. By contrast, the chain mail mesh 100 has relatively smooth contact surface(s) imparted by the flat or substantially flat surfaces of the employed links in the external top and bottom XY plane surfaces, which when contacted with and/or moved over a body part (such as the skin of a hand) of the human, has a much higher contact area with such body part and a much smoother and pleasant texture (or feel), thus providing a soothing effect to the body part.

More specifically, in accordance with an aspect of the present invention, a chain mail mesh 100 in the form of a sheet 102 is illustrated in FIG. 1, wherein a plurality of interconnecting, polygonal links 104 are interconnected to define the sheet 102. The chain mail mesh 100 comprises the interconnecting, polygonal links 104 suitably interconnected to define the sheet 102. The sheet 102 has a predetermined length (ML), a predetermined breadth (MB), a predetermined thickness (MT) and a predetermined weight (MW). Each of the interconnecting, polygonal links 104 have at least one degree of freedom of movement in at least one direction with respect to its neighbouring polygonal links and have a length (LL), a breadth (LB), a thickness (LT) (FIG. 2C), and weight (LW). Further, each of the interconnecting, polygonal links 104 are interconnected to at least one neighbouring interconnecting polygonal link 104, which combine to form an operative upper surface 102A and an operative lower surface 102B of the sheet 102. At least a portion of at least one of the operative upper surface 102A and the operative lower surface 102B of the sheet 102 are configured to be flat or substantially flat such that they generally feel smooth, which can produce a calming effect when contacted with or moved over, or combinedly contacted with and moved over a human's body portion which is apt to sense of touch. In an embodiment, the interconnecting, polygonal links 104 may be interconnected to the at least one neighbouring interconnecting polygonal link directly. In another embodiment, the interconnecting, polygonal links 104 may be connected to at least one neighbouring interconnecting polygonal link via an intermediate connecting member (not shown in the figures).

In accordance with an embodiment of the present invention, the length (ML) and the breadth (MB) of the sheet 102 may be independently in the range of 50 mm to 250 mm, and the thickness (MT) of the sheet may be in the range of 1 mm to 25 mm, preferably in the range of 10 mm to 14 mm, when the sheet is placed on a substantially flat surface, whereas the length (LL), and the breadth (LB) of the interconnecting, polygonal links may be independently in the range of 2 mm to 30 mm, preferably in the range of 10 mm to 14 mm, and the thickness (LT) of the interconnecting, polygonal links is in the range of 1 mm to 25 mm, preferably in the range of 10 mm to 14 mm.

Further, the weight (MW) of the sheet 102 may be varied. In particular, the weight of the sheet 102 may be varied by employing heavy or light interconnecting, polygonal links 104 and polygonal end cap links 106. In an embodiment, a mix of heavy and light interconnecting, polygonal links 104 may be employed. In another embodiment, all the interconnecting, polygonal links may have the same weight. In yet another embodiment, the weight of the interconnecting, polygonal links and that of the polygonal end cap links may be the same or different. In an embodiment, the weight (LW) of the interconnecting, polygonal links 104 may be in the range of 0.1 grams to 25 grams. In another embodiment, the weight (LW) of the interconnecting, polygonal links 104 may be in the range of 0.1 grams to 2 grams. In one embodiment, the weight (LW) of the interconnecting, polygonal links 104 may be within the range of 0.18 grams and 0.17 grams.

In accordance with an embodiment, the weight (MW) of the sheet 102 may be in the range of 10 grams to 1,000 grams. In another embodiment, the weight (MW) of the sheet 102 may be in the range of 50 grams to 100 grams. In one embodiment, the weight (MW) of the sheet may be within the range of 55 grams and 60 grams.

In accordance with an embodiment of the present invention, the interconnecting, polygonal links 104 may have a square shape as depicted in FIG. 2A, FIG. 2B and FIG. 2C. The interconnecting, polygonal links 104 may comprise at least two lower horizontal connector members (1042, 1044), which define an operative lower surface 104B of the interconnecting, polygonal links 104, and at least two upper horizontal connector members (1046, 1048), which define an operative upper surface 104A of the interconnecting, polygonal links 104. Further, the at least two lower horizontal connector members (1042, 1044) are connected to the at least two upper horizontal connector members (1046, 1048) at corner posts (1050) to define a continuous link.

In accordance with another embodiment of the present invention, the interconnecting, polygonal links 104 may have a square shape as depicted FIG. 4A and FIG. 4B, wherein, the interconnecting, polygonal links 104 comprises at least two lower horizontal connector members (1042, 1044), which define an operative lower surface 104B of the interconnecting, polygonal links 104, and at least two upper horizontal connector members (1046, 1048), which define an operative upper surface 104A of the interconnecting, polygonal links 104. Further, the at least two lower horizontal connector members (1042, 1044) are connected to the at least two upper horizontal connector members (1046, 1048) at corner posts (1050) to define an incessant link, and a lower transverse intermediate connector member 1052 is disposed between and connected to the at least two lower horizontal connector members (1042, 1044) and an upper transverse intermediate connector member 1054 is disposed between and connected to the at least two upper horizontal connector members (1046, 1048). The various corners and edges in the illustrated embodiment are shown as forming 90 degree angles, however, in an embodiment the corners and edges may comprise a fillet or chamfer to improve the overall smoothness of the swatch.

The provision of the lower transverse intermediate connector member 1052 and the upper transverse intermediate connector member 1054 may further increase the surface area and also the smoothness of the operative upper surface 104A and the operative lower surface 104B of the interconnecting, polygonal links 104 and that of the sheet 102 and at the same time may provide strength to the interconnecting, polygonal links 104.

The swatch may include a macro-smoothness which refers to the texture of the swatch as it feels to the user while the swatch is moved over the skin of the user and a micro smoothness which refers to the smooth texture of the touchable surface of the individual links which are free of sharp protrusions or corners. For example, the touchable surface of the links although not mirror smooth may not have protrusions from the bulk of the link of greater than 0.1 mm, with any another dimension within 75 degrees of surface of the link of less than 0.1 mm. The macro-smoothness, in addition to the smoothness of the touchable surface of the links, depends on the shape of the links, their number per area and also on the gaps between the links.

In accordance with the present invention, the interconnecting, polygonal links 104 (FIG. 2A, FIG. 2B, FIG. 2C, FIG. 4A, and FIG. 4B) may have the operative upper surface 104A, the operative lower surface 104B, and one or more substantially smooth edges 104C, The operative upper surface 104A, the operative lower surface 104B and the one or more substantially smooth edges 104C may have a shape which may be selected from the group consisting of flat or planar, concave, convex, and any combinations thereof. Any other shape is also well within the ambit of the present invention provided the shape provides a smooth feel. In an embodiment, the operative upper surface 104A and the operative lower surface 104B of the interconnection polygonal links each have a flat surface.

In accordance with an embodiment of the present invention, at least one layer of polygonal end cap link 106 is connected to an outer most layer 104D of the interconnecting, polygonal links 104 of the sheet 102. In an embodiment, the polygonal end cap links 106 may be the same as that of the interconnecting, polygonal links 104. In another embodiment, the polygonal end cap links 106 are different from that of the interconnecting, polygonal links 104. In yet another embodiment, at least some of the polygonal end cap links 106 may be the same as that of the interconnecting, polygonal links 104 and some of the polygonal end cap links 106 are different from that of the interconnecting, polygonal links 104 in a given sheet 102. In the present context, the meaning of different or same polygonal end cap links 106 is that the structure or design or form of the polygonal end cap links 106 is same as that of the interconnecting, polygonal links 104 or the structure or design or form is different as compared to that of the interconnecting, polygonal links 104. Any other shape of the polygonal end cap links 106 may include a ring or a continuous loop-like structure. In the present context, the meaning of different or same polygonal end cap links 106 may also mean that the composition of the interconnecting, polygonal links 104 or the material of make of the interconnecting, polygonal links 104 may be different or same.

In accordance with an embodiment of the present invention, the interconnecting, polygonal links 104 may be in the form of polygons, wherein the polygon is at least one selected from the group consisting of a three-sided polygon, a four-sided polygon, a five-sided polygon, and a six-sided polygon. The shape of the interconnecting, polygonal links 104 may be at least one shape selected from the group consisting of a triangle, a square, a rectangle, a hexagon and any combinations thereof. In an embodiment, the sheet 102 may comprise a mix of links with some interconnecting, polygonal links 104 being four-sided polygons, and some others being six-sided polygons. In another embodiment, the sheet 102 may comprise interconnecting, polygonal links 104 which are a mix of three-sided and four-sided polygons. In an embodiment, the interconnecting, polygonal links 104 may have a square shape when viewed from the top. In another embodiment, the interconnecting, polygonal links 104 have a rectangular shape when viewed from the top.

The interconnecting, polygonal links 104 and the polygonal end cap links 106 may be each independently manufactured from a material selected from the group consisting of plastic, elastomer, thermoplastic, metal, and any combinations thereof. The choice of the material depends on the drape of the sheet 102 to be achieved, the body portion over which the sheet 102 is to be used, and the weight of the sheet 102 to be achieved. In an embodiment, the interconnecting, polygonal links 104 and the polygonal end cap links 106 are each independently manufactured from plastic, preferably a thermoplastic material such as a polyolefin thermoplastic including but not limited to homopolymer polyolefins, random copolymer polyolefins and impact copolymer polyolefins. The plastic material may be coloured or alternatively a paint coating may be employed. The plastic material may be metal coated. The drape, the weight, the shape, and the structure and design of the interconnecting, polygonal links 104 are selected so as to provide a smooth feel when contacted with the body portion and provide stress relief when played or engaged with the same. In an embodiment, the interconnecting, polygonal links 104 and the polygonal end cap links 106 are each independently manufactured from plastic. In an embodiment, the interconnecting, polygonal links 104 and the polygonal end cap links 106 are each independently made of thermoplastic material.

In a specific embodiment, the chain mail mesh 100 may include a plurality interconnecting, polygonal links 102 suitably interconnected to define a sheet 102 having a length (ML), a breadth (MB), a thickness (MT), and weight (MW), each of the interconnecting polygonal link 104 comprising at least two lower horizontal connector members (1042, 1044), at least two upper horizontal connector members (1046, 1048), at least one lower transverse intermediate connector member 1052 disposed between and connected to the at least two lower horizontal connector members (1042, 1044), and at least one upper transverse intermediate connector member 1054 disposed between and connected to the at least two upper horizontal connector members (1046, 1048), wherein the at least two lower horizontal connector members (1042, 1044) along with the at least one transverse intermediate connector member 1052 define an operative lower surface 1056 of the interconnection polygonal link 104, wherein the at least two upper horizontal connector members (1046, 1048) along with the at least one transverse intermediate connector member 1054 define an operative upper surface 1058 of the interconnection polygonal link 104, wherein the at least two lower horizontal connector members (1042, 1044) being connected to the at least two upper horizontal connector members (1046, 1048) at corner posts 1050 to define an incessant link, wherein each of the interconnecting polygonal link 104 is made of thermoplastic material and having a length and a breadth in the range of 10 mm to 14 mm, independently, a substantially square shape, each of the interconnecting, polygonal links being similar in structure, dimensions, and shape, wherein each of the interconnecting polygonal link 104 is interconnected to at least one neighbouring interconnecting polygonal link 104 combine to form an operative upper surface 102A and an operative lower surface 102B of the sheet 102, wherein the number of interconnecting, polygonal links 104 being in the range of 5 to 15 along the length and the width of the sheet 102 independently, wherein the sheet 102 is either having a substantially rectangular configuration or a substantially square configuration wherein the sheet 102 is laid on a flat surface, wherein at least a portion of at least one of the operative upper surface 102A and the operative lower surface 102B of the sheet generally feels smooth, which produce a calming effect when contacted with or moved over, or when contacted with and moved over a human's body portion which being apt to sense of touch, and wherein the sheet 102 includes at least one layer of polygonal end cap link 106 connected to an outer most layer of the interconnecting polygonal link 104 of the sheet 102, the polygonal end cap link 106 being same as that of the interconnecting polygonal link 104 or the polygonal end cap link 106 being different from that of the interconnecting polygonal link 104.

In an embodiment, at least a portion of the sheet 102 is bendable in at least one direction selected from an operative upward direction 102C of the operative upper surface 102A of the sheet 102, an operative downward direction 102D of the operative lower surface 102B of the sheet 102 and a combination thereof. In particular, the sheet 102 has a predetermined drape coefficient similar to a cloth or a fabric, but at the same time, the sheet 102 has a predetermined radius of curvature when the sheet 102 is placed on a support. This, in turn, means that the sheet 102 though bendable in operative upper and lower directions, is not completely flexible as a cloth or fabric. In an embodiment, the sheet 102 has a predetermined drape coefficient. In accordance with an embodiment of the present invention, the drape coefficient of the sheet 102 may be the same along the length (ML) and the breadth (MB) of the sheet 102. In another embodiment, the drape coefficient of the sheet 102 may be different along the length (ML) and the breadth (MB) of the sheet 102. Further, the thickness (MT) of the sheet 102, when the sheet is in draped configuration, is different from the thickness (MT) of the sheet, when the sheet 102 is placed on a substantially flat surface.

Owing to the above, the bendability and the radius of curvature of the sheet 102, the sheet 102 drapes when contacted with or moved over, or when contacted with and moved over a human's body portion and substantially conforms to the shape of the body portion, wherein the operative lower surface 102B of the sheet 102 in contact with the body portion provides a calming effect thereto.

In order to facilitate the draping of the sheet 102, the interconnecting, polygonal links 104 within the sheet 102 are spaced apart with a gap 102E in an at rest state therebetween, the gap 102E being in the range of 0.2 mm to 10 mm, more preferably in the range of 0.5 mm to 4 mm, thereby configuring a loose hinge between two consecutive interconnecting, polygonal links 104. A minimum, smaller gap of 0.1 mm, preferably of 0.2 mm is envisioned to avoid pinching or catching of hair. The gap 102E provides the necessary flexibility and hence bendability and the drape to the sheet 102. At the same time, the shape of the interconnecting, polygonal links 104 along with the dimensions and the gap 102E also make the sheet 102 resistant to drape further than a predetermined curvature. It has been discovered by the Applicant that the sheet 102 having the above configuration when contacted with a body portion of a human provides a calming effect thereto. Further, owing to the gaps, and the dimensions of the interconnecting, polygonal links 104, at least a portion of the sheet 102 is skewable in at least one direction substantially parallel to a plane of the sheet 102. In the preferred embodiment the XY area of the gaps is smaller than the solid XY area of the link 104, when the sheet is in a configuration having its smallest XY area.

In an embodiment, the dimensions, the shape, the material of make of the sheet 102 are chosen such that the sheet 102 when displaced is capable of generating an acoustic spectrum during typical play or movement between the fingers or two human hands. In an embodiment, the acoustic spectrum has at least one frequency in the range of 20 Hz to 20,000 Hz.

The chain mail mesh 100, the interconnecting, polygonal links 104 and the polygonal end cap links 106 may be manufactured by any known method in the art. For example, the chain mail mesh 100, the interconnecting, polygonal links 104 and the polygonal end cap links 106 may be manufactured by at least one method selected from the group consisting of 3D printing, injection molding (for example, continuous plastic injection molding), snap fitting, casting, such as zinc casting, and any combinations thereof. In an example, the interconnecting, polygonal links may be injection molded separately and then snap-fitted to configure the sheet 102.

In accordance with another aspect, a method of reducing stress or otherwise improving mental state in humans employing the chain mail mesh 100 hereinabove is disclosed. The method comprises the steps of contacting with or moving over, or combinedly contacting with and moving over a human's body portion which being apt to sense of touch, the chain mail mesh 100, wherein the chain mail mesh 100 intermittently contacts with nerve endings of the body portion thereby provide a calming effect thereto.

In accordance with yet another aspect, a process for reducing stress in humans is disclosed, wherein the process comprises the steps of holding the chain mail mesh 100, in hands of a human, contacting the chain mail mesh 100 with a body portion of the human and/or moving the chain mail mesh 100 over the body portion of the human such that the operative lower surface 102B or the operative upper surface 102A contacts with nerve endings of the body portion and thereby provide a calming effect thereto, and repeating the above steps more than once to reduce the stress in humans.

In accordance with the present invention, the body portion with which the chain mail mesh 100 is contacted may be at least one selected from the group consisting of hand, wrist, head, forehead, face, shoulder, back, chest, neck, finger, calf, knee, thigh, hip, waist, foot, heel, ankle, buttock, leg, skin, and stomach, and is not limited to these. The preferred boy part comprises fingers and at least part of one or two hands.

Though the present invention has been described with reference to contacting with and/or moving over, the chain mail mesh, the body part of a human, there may be other ways that may be employed to engage with the chain mail mesh. For example, the chain mail mesh of the present invention may be simply draped over the hand(s), forearm, leg, or foot. The chain mail mesh may be rattled to emit a noise/sound, which may be stress relieving for some. Further, the chain mail mesh may be rubbed against skin or wrapped on a finger or may be placed on a hard surface and rest a body part or skin over it or may be played with by placing it in a pocket.

Further, the surfaces, the operative upper surface and the lower operative surface of the interconnecting, polygonal links and that of the sheet 102 may be made somewhat rough rather than being smooth as described hereinabove, which may be used for playing with.

The present invention may also be used to better observe signs of stress and other underlying feelings during psychological therapy sessions, interrogations, job interviews and the like. Applicant has observed that subjects holding the present invention tend to play with it more frequently and with more intensity during more stressful moments. The visual and audible indicators are often somewhat proportional to stress, anxiety or similar feelings, especially when correlated with the same subject.

The present invention is now described with reference to the following examples which are provided to illustrate the present invention more clearly and not to limit the scope thereof.

EXAMPLE

Four types (S. No. 1-4) of chain mail mesh were evaluated by a group of test subjects and the feedback was noted. The attributes of the different types of the chain mail mesh are summarized in Table I below.

TABLE I

| S. No. | CMM | MAT | COL | ML | MB | MT | MW | LL | LB | LT | LW |
|---|---|---|---|---|---|---|---|---|---|---|---|
| 1 | I | P | BL | 200 | 200 | 3 | 60 | 11 | 11 | 3 | 0.18 |
| 2 | II | P | WH | 202 | 202 | 3 | 55 | 12 | 12 | 3 | 0.17 |
| 3 | III | P | PI | 60 | 60 | 3 | 5 | 12 | 12 | 3 | 0.20 |
| 4 | IV | M | GR | 120 | 90 | 1 | 53 | 10 | 10 | 1 | 0.31 |

CMM—Chain mail mesh
MAT—Material of make of the chain mail mesh
COL—Colour of the chain mail mesh
ML—Length of the chain mail mesh (mm)
MB—Breadth of the chain mail mesh (mm)
MT—Thickness of the chain mail mesh (mm)
MW—Weight of the chain mail mesh (grams)
LL—Length of the interconnecting polygonal link (mm)
LB—Breadth of the interconnecting polygonal link (mm)
LT—Thickness of the interconnecting polygonal link (mm)
LW—Weight of the interconnecting polygonal link (grams)
P—Plastic
M—Metal
BL—Black
WH—White
PI—Pink
GR—Grey The feedback regarding the stress relief/reduction, and the possibility of the use of the chain mail mesh type for stress relief/reduction is summarized in table II herein below:

TABLE II

| S. No. | A | B |
|---|---|---|
| I | Colour | |
| | Black | 58 |
| | White | 8 |
| | Pink | 0 |
| | Metal | 50 |
| II | Physical | |
| | Weight | 8 |
| | Colour | 42 |
| | Feel | 67 |
| | Shape | 33 |
| | Size | 42 |
| | Sound | 33 |
| | Sound | 8 |
| | Structure | 83 |
| | Texture | 42 |
| | Weight | 42 |

TABLE II-continued

| S. No. | A | B |
|---|---|---|
| III | Activity | |
| | Play | 100 |
| IV | Engaging? | |
| | Engaging | 92 |
| | Non-engaging | 8 |
| V | Relaxing? | |
| | Relaxing | 42 |
| | Non-relaxing | 58 |
| VI | Feel on skin | |
| | Relaxing | 33 |
| | Non-relaxing | 67 |
| VII | Noise/Sound | |
| | Noise irritating | 8% |
| | Null | 33% |
| | Very good noise | 8% |
| VIII | Which colour do you want? | |
| | Any | 8 |
| | Brown shiny | 8 |
| | Grey | 8 |
| | NA | 68 |
| | Yellow | 8 |
| IX | Length/breadth | |
| | 10-15 cm | 84 |
| | 10-15 cm or greater | 8 |
| | 25-50 cm | 8 |
| X | Use for what? | |
| | Keep Around | 25 |
| | Play | 83 |
| | Sound generator | 8 |
| | Stress buster | 17 |
| XI | Use for? | |
| | Teacup | 8 |
| | Base for showpiece | 8 |
| | Coaster for hot surface, | 8 |
| | Eye exercise | 8 |
| | For jogging on it | 8 |
| | Laptop screen cover | 8 |
| | Massage | 8 |
| | Massager | 8 |
| | Mouse pad | 17 |
| | Multiplevisual patterns & shapes | 8 |
| | Place hot containers | 8 |
| | Scrubbing | 8 |
| | Sitting on it | 8 |
| | Tea coaster | 8 |
| | Temperature variation | 8 |
| | Wall hanging | 8 |
| XII | Shape and color | |
| | Circular | 24 |
| | Colorful, make pics with it | 8 |
| | Metal | 8 |
| | Not answered | 42 |
| | Smoot surface | 8 |
| | Steel | 8 |
| | Triangular shape | 8 |
| | Visual effects, change direction to get different images | 8 |
| XIII | Buying | |
| | Buy | 83 |
| | Not buy | 17 |
| XIV | Price at which you may buy (USD) | |
| | 1 | 42 |
| | 2 | 17 |
| | 4 | 17 |
| | 6 | 8 |
| | 4 to 6 | 16 |

A-Attribute
B-is the percentage of people interested in the attribute

Inference from Table II:

From Table II it is evident that the chain mail mesh made of plastic with black color and having a structure or configuration as described in the description above was most favored and was found to be useable and stress-reducing when employed a majority of the members of the group.

Manufacturing method: The swatch may be made by any suitable methods including but not limited to 3D printing, UV resin printing, injection molding, zinc casting, and co-moulding. For example, parts may be printed together to save costs. Parts may be snapped together or better fused in place to minimize choking hazard of links. While the main links are rigid, co-molding with an elastomer or other flexible or soft to the touch material may be employed according to an embodiment. In an embodiment, the links may be foamed or otherwise below theoretical density of their material. Secondary manufacturing treatment may include but is not limited to coating, finishing, partial finishing, grinding, polishing, solvent treatment, etch, flash removal, rounding of sharp edges, thinning, and separating bound links. Manufacturing does not include metal welded rings other than optionally as a connector for the links defined herein.

The present invention has been described with reference to the specific embodiments and drawings, which are meant for the purpose of describing the invention and its features and not to limit the scope of the present invention. It may be obvious that the invention may be varied in numerous ways. Such variants should not be regarded as a departure from the essence and scope of the present invention, and all such modifications as would be obvious to one skilled in the art are intended to be included within the scope of the present inventions and claims appended herein. While a very specific link is shown, it is merely one illustrative embodiment of the present invention.

I claim:

1. A method for detecting or reducing anxiety, fidgeting, or stress type symptoms in a human, the method comprising:
   providing a device comprising:
      a flexible swatch comprising a plurality of discrete, flexibly connected interconnecting links, wherein the swatch forms a sheet having a maximum at rest XY area from 10 cm$^2$ to 400 cm$^2$, wherein the swatch can bend sufficiently such that at least 3 of the interconnecting links that are not directly interconnected can touch, and
      wherein the swatch contains at least one type of link having a substantially smooth external upper and lower surface such that all or a majority of an X-Y plane area of the external upper and lower surface comprises a flat or substantially flat portion, wherein the link includes only rounded touchable corners and free of any sharp external edges, placing the device on a body portion of the human which is apt to sense of touch, and moving the device over the body portion,
wherein said device intermittently contacts skin areas near nerve endings of said body portion thereby providing a calming effect to the human.

2. The method according to claim 1, wherein the placing of the device on the body portion of the human includes holding the device in a hand; and
contacting the device with a skin portion of said hand and moving the device over the skin portion of said hand such that at least one of the lower surface and the upper surface stimulates nerve endings of said skin portion and thereby provide the calming effect to the human.

3. The method according to claim 1, wherein the placing the device on the body portion of the human includes the human moving at least some of their fingers over the lower or upper surface or both to feel a relief pattern formed by a combination of gaps and smooth surfaces of the device, and the human moves the device in three dimensions to maximize contact with their skin areas.

4. The method according to claim 3, wherein the human moves the device from hand to hand.

5. The method according to claim 3, wherein the body portion is a first hand of the human, and the human is holding the device with a second hand, wherein the placing of the device on the body portion of the human includes contacting the device with a skin portion of said first hand and moving the device over said skin portion of said first hand such that at least one of the lower surface and the upper surface stimulates nerve endings of said skin portion thereby inducing the human to increase rate or frequency or both of motion of the device, and
wherein the method further comprises observing the increase in rate or frequency of motion of the device visually, audibly or both.

6. The method of claim 3, wherein the human is a person diagnosed with attention deficit hyperactivity disorder.

7. The method of claim 3, wherein the human is a person diagnosed with autism.

8. The method of claim 3, wherein the human is a person undergoing psychological therapy, an interview, an interrogation, or a lie detection procedure.

9. The method of claim 1, wherein the human is a person undergoing psychological therapy, an interview, an interrogation, a lie detection, or a job interview, and wherein the body portion is a first hand of the human, and the human is holding the device with a second hand, wherein the placing of the device on the body portion of the human includes contacting the device with a skin portion of said first hand and moving the device over said skin portion of said first hand such that at least one of the lower surface and the upper surface stimulates nerve endings of said skin portion thereby inducing the human to increase rate or frequency or both of motion of the device, and
wherein the method further comprises observing the increase in rate or frequency of motion of the device visually, audibly or both.

10. The method of claim 9, wherein the swatch comprises a square or rectangle with missing corner pieces.

11. The method of claim 1,
wherein the link is free of any protrusions greater than 0.1 mm,
wherein the link is connected to at least three other links, and
wherein the link has a length (LL) and breadth (LB) of within 0.3 cm to 2.5 cm and a thickness (LT) of 0.5 mm to 20 mm.

12. The method of claim 1, wherein the link is free of any protrusions of greater than 0.1 mm, and wherein an edge transitioning to a side surface connecting said upper and lower surfaces is a curved edge.

\* \* \* \* \*